United States Patent [19]

Bakx et al.

[11] 4,135,881
[45] Jan. 23, 1979

[54] METHOD AND APPARATUS FOR DETERMINING THE THERMAL CRACKING BEHAVIOR OF HYDROCARBON FEEDS FOR CRACKING FURNACES

[75] Inventors: Cornelis A. C. L. Bakx; Jacobus T. J. van Goolen; Jacobus Jansen; Hubertus G. Kuiper, all of Geleen, Netherlands

[73] Assignee: Stamicarbon, B.V., Geleen, Netherlands

[21] Appl. No.: 839,741

[22] Filed: Oct. 5, 1977

[30] Foreign Application Priority Data

Oct. 6, 1976 [NL] Netherlands .................. 7611006

[51] Int. Cl.² ............................................ G01N 31/12
[52] U.S. Cl. .......................... 23/230 PC; 422/68; 422/89
[58] Field of Search ............ 23/230 PC, 253 PC

[56] References Cited

U.S. PATENT DOCUMENTS

| | | | |
|---|---|---|---|
| 3,205,045 | 9/1965 | Von Lossberg | 23/230 PC X |
| 3,703,355 | 11/1972 | Takahashi et al. | 23/230 PC |
| 3,996,003 | 12/1976 | Pine et al. | 23/230 PC |

Primary Examiner—Robert M. Reese
Attorney, Agent, or Firm—Cushman, Darby & Cushman

[57] ABSTRACT

A method and apparatus for determining in a laboratory the thermal cracking behavior of hydrocarbon feedstocks which are to be used in industrial cracking furnaces. The apparatus used includes an evaporation assembly and a cracking furnace assembly. A sample of hydrocarbon feedstock is first vaporized, then thermally cracked, and the cracked products are then fed to gas chromatography analytical equipment for analysis.

19 Claims, 1 Drawing Figure

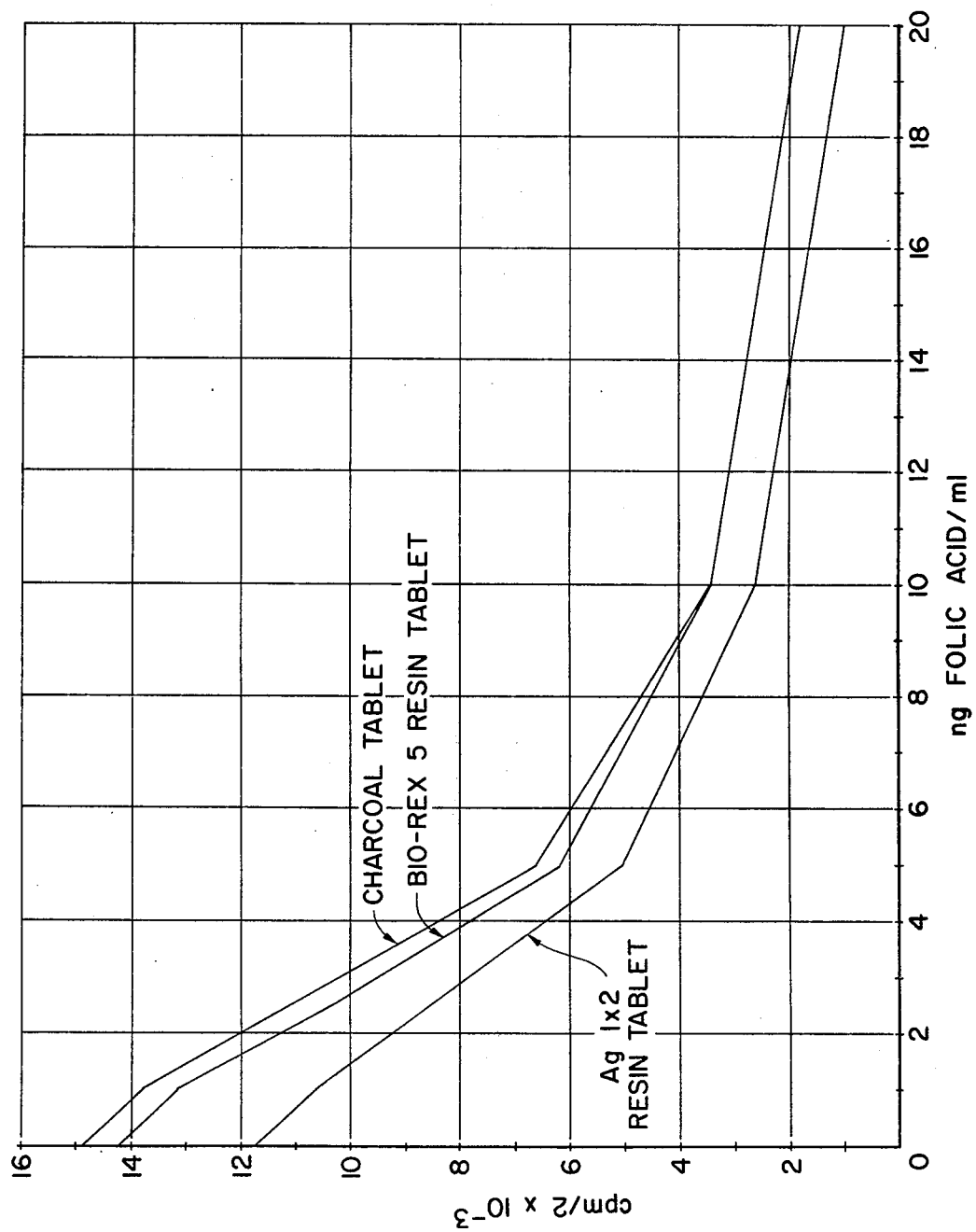
FIG._1.

METHOD AND APPARATUS FOR DETERMINING THE THERMAL CRACKING BEHAVIOR OF HYDROCARBON FEEDS FOR CRACKING FURNACES

This invention relates to and provides an analytical method and apparatus for the determination of a "cracking behavior" of hydrocarbon feedstocks, adapted for laboratory use.

BACKGROUND OF THE INVENTION

In industrial practice for the cracking of hydrocarbon feedstocks, typically large cracking furnaces are used and the feedstock is exposed to high temperatures, in the "cracking" range, and the process is typically carried out in the presence of steam. Because the hydrocarbon feedstocks have varying compositions, it is important to determine in a simple and efficient way the optimum cracking conditions required to obtain the products desired. For instance, it is frequently desired to convert a hydrocarbon feedstock composed of C-5 through C-12 hydrocarbons into cracked products such as ethylene, propylene, methane etc.

However, depending upon the composition of the particular feedstock employed under a given set of cracking conditions, more-or-less of the desired aromatic fractions will be obtained, and the yield thereof will be maximized only if optimum cracking conditions are employed.

It is therefore important that prior to initiating such industrial cracking furnace operations, such optimum conditions first be established for each hydrocarbon feedstock to be introduced therein.

Currently, such optimum conditions are sometimes computed through the means of mathematical models based upon data previously collected in prior cracking experience. However, such computations are in practice somewhat unreliable. Alternatively, it has also been the practice to develop data for predicting the cracking behavior of a given hydrocarbon feedstock by the use of semi-technical scale test cracking furnaces. While the data obtained from such procedures is usually more reliable than that computed from a mathematical model, such tests at the semi-technical scale level are nonetheless time consuming, somewhat complicated, and the test unit is not readily adapted for simple laboratory use.

DESCRIPTION OF THE INVENTION

It is therefore an object of the present invention to provide a method and apparatus, adapted for use at a laboratory scale level, for determining the cracking behavior of hydrocarbon feedstock in a rapid and efficient way. It is a further object to provide such a method and apparatus which will yield data closely representative of the way in which the cracking reaction for the feedstock under examination will proceed in an industrial cracking furnace. As used herein, the term "cracking behavior" refers to the overall and composite course of the cracking reactions which will take place in an industrial cracking furnace for a given hydrocarbon feedstock and at a given set of conditions.

In particular, the present invention provides a method and apparatus for determining cracking behavior of a hydrocarbon feedstock using samples of as little as 20 microliters or less, an admixture with an inert gas (e.g., nitrogen, argon, helium) suitable for gas chromatographic analysis to identify the cracked products.

By varying the temperature employed in a monotubular furnace of capillary dimensions, in successive tests the optimum conditions for operation of the cracking furnaces may be readily determined.

According to this invention, it has been found that in order to achieve reproduceability of the cracked product production between the operation of the capillary-size tubular furnace used herein and an industrial-size cracking furnace it is necessary that:

(a) there also be used a step of evaporating the sample of the hydrocarbon feedstock;

(b) means for an admixing of such vaporized feedstock samples with a determined quantity of an inert gas (calculated so as to reproduce the partial pressure of the feedstock and cracked products vapor composition which will ultimately be present in the industrial-sized furnace); and (c) propelling the mixed inert gas/hydrocarbon feedstock vapors into the capillary-size tube of the test furnace.

Typically, residence time for the sample in a mono-tubular furnace of capillary dimensions as used herein will be in the range of 0.1 to 1 seconds, preferably, in a range requiring no more than 0.2 to 0.5 seconds (depending on the industrial furnace simulated by the laboratory equipment).

The vapors removed from such a test furnace are then delivered directly to gas chromatograph analytical instruments for determination of their composition by known means.

The mono-tubular furnace of capillary dimensions is comprised of sections and the temperature in each section can be controlled and maintained individually. Two flows of inert gas are used in moving the sample to be tested through the apparatus. One flow which will be referred to herein as the "main gas" is used to propel the mixed inert gas/hydrocarbon feedstock vapors from the evaporating chamber to the mono-tubular furnace of capillary dimensions.

The second flow which will be referred to herein as the "diluting gas" is used both to adjust the partial pressure of the hydrocarbon feedstock sample and along with the main gas to transfer the hydrocarbon feedstock vaporous sample and the resultant cracked products through the said test furnace and into the analytical equipment.

The analytical equipment consists of one or more gas chromatographs, but also other analytical instruments suitable for the determination of the composition of the cracked products can be used. In the method and apparatus of the present invention, an inert gas, such as nitrogen, argon, helium is used as the diluting gas instead of steam which is used for diluting in industrial thermal cracking furnaces because steam would interfere with the gas chromatographic analysis of the resultant cracked products.

The reaction chamber of the said mono-tubular furnace is a capillary-sized tube and is lodged in a block of metal which has a good heat transfer coefficient and which will not react at the cracking temperature with the material of the capillary-sized tube. An example of such a metal is Incoloy. The metal block containing the capillary-size-tubular reaction chamber is heated by means of electric coils. Preferably, the block is comprised of sections which can be heated individually.

The material used in making the capillary-size-tubular reaction chamber must not react with either the hydrocarbons of the cracking reaction or with the surrounding heat-conducting block and therefore must be constructed of a catalytically inert material. Suitable catalytically inert materials of construction for the capillary-size-tubular reaction chamber include: Silicates including ceramic materials and quartz; sintered metal compounds with carbon and/or silicon; inactive metals, such as titanium, columbium, gold, zirconium, and inactive alloys of these metals; and also alloys of the metals from group IB of the Periodic Table. Other materials rendered inactive by physical or chemical means may also be used.

One of the advantages associated with the use of the method in accordance with the present invention is the inherent rapid method of analysis because the entire product range is made available for analysis at the same time. This eliminates the time-consuming process of obtaining a sufficient liquid sample of the cracked process, and the separation of the liquid sample into its constituents and the analyses thereof. Another advantage is that the apparatus and method are suitable for use in a laboratory. Additionally, only a small sample of raw material is required for the test which facilitates use in the laboratory. A further advantage is that the entire product range from the thermal cracking is available at the same time with pyrolyses fuel oil as the final fraction. It is therefore quite simple to carry out a measurement for obtaining a mass balance. Additionally, the method of the present invention is significantly less expensive than the prior methods.

In accordance with the method of the present invention, a 0.5 to 20 microliters sample of the hydrocarbon feedstock to be examined is injected into the evaporating chamber. The dimensions of the evaporating chamber are chosen in relation to the volume of the sample, so that the volume of the evaporating chamber is big enough to contain the evaporated sample. The preferred sample is about 5 microliters. The temperature in the evaporating chamber will range between about 350° and 450° C. with the preferred temperature being about 400° C.

If the cracking behavior of a gaseous substance as opposed to a liquid sample is to be determined, the gas is not injected into the evaporating chamber through the septum opening but is injected directly into the "main gas" feed-line and then into the evaporating chamber for dilution.

The capillary-size-tubular reaction chamber of the furnace has an internal diameter of between about 0.60 and about 3.00 mm. and is preferably about 1 mm. The furnace temperature will range, as needed, between about 700° and about 900° C.

The metal block which encloses the capillary-size-tubular reaction chamber is constructed in sections with each section heated separately in order to develop a temperature gradient in the capillary-size-tubular reaction chamber if desired. The length of the reaction chamber may vary from about 20 to about 250 cm. and is preferably about 30 to about 120 cm. in length.

DESCRIPTION OF THE DRAWINGS

By way of example the invention will be illustrated by reference to a drawing.

The drawing is directed to the apparatus of the present invention.

The apparatus used in carrying out the method of the present invention is comprised of an evaporation assembly, A of the drawing, and a mono-tubular furnace of capillary dimensions assembly, B of the drawing.

The mono-tubular furnace of capillary dimensions, B, as shown in the drawing consists of three sub-sections with each sub-section being heated separately. It is to be understood that said mono-tubular furnace section may be constructed of any number of sub-sections and it is for illustrative purposes only that the drawing shows the said mono-tubular furnace section to be comprised of three sub-sections. It is also to be understood that each sub-section is essentially identical and each has its own individual thermocouple assembly, electrical connections for heating, and electrical heating elements and it is for illustrative purposes only that the drawing shows a thermocouple assembly, electrical connections for heating, and electrical heating elements in only one of three sub-sections. It is also to be understood that a thermocouple assembly, electrical connections for heating, and an electrical heating element are also provided for the evaporation assembly, A, even though not shown in the drawing.

The evaporation assembly, A, is comprised of a septum opening 1 sealed with silicone rubber which is connected to an evaporating chamber 3. A gas feed line 2 is connected to the inlet of the evaporating chamber. The evaporating chamber 3 is enclosed by a heating block 4. A second gas feed line 5 is connected to the outlet of the evaporating chamber.

The evaporation assembly, A, is connected to the said mono-tubular furnace assembly, B.

The said mono-tubular furnace assembly, B, is comprised of the capillary-size-tubular reaction chamber 6 constructed of a catalytically inert material. The reaction chamber tube 6 is enclosed by a metal supporting block 7 which is constructed of a metal with a good heat transfer coefficient. In turn, the supporting block 7 is enveloped by an electric heating block 8. The electric heating block consists of an electrical heating element 10 which is provided with electrical connections for heating 14. A thermocouple assembly 13 is embedded in the heating block 8. Heating means 11 are provided at the end of the cracking furnace section nearest the outlet of the furnace tube 6 to provide for an additional incremental increase in temperature, if needed.

The outlet of the mono-tubular furnace assembly B has connection means 12 for connecting the outlet of the reaction chamber tube 6 with gas chromatography analytical equipment.

Both, the evaporation assembly A, and mono-tubular furnace assembly, B, are covered with an insulation material 9.

The method of the present invention is carried out, with reference to the drawing, by injecting a liquid sample of the hydrocarbon feedstock through the septum opening 1 and into the evaporating chamber 3. The liquid sample is heated and vaporized. Inert gas is fed through the gas feed line 2 and propels the vaporized gas which is simultaneously being mixed with a second feed of inert gas into the capillary-size-tubular reaction chamber 6. Said additional feed of inert gas is fed into the evaporating chamber 3 through the second gas feed line 5 in order to dilute the vaporized sample of hydrocarbon feedstock at the same time as the vaporized sample is propelled into the furnace assembly, B.

The mixed inert gas/hydrocarbon feedstock vapors are propelled into the mono-tubular furnace assembly B wherein said sample is cracked. Immediately after leaving the cracking furnace, the cracked products are fed to gas chromatography analytical equipment for analysis.

EXAMPLE

The efficacy of the present invention is demonstrated by the following example. Paraffin naphtha was selected as the raw material. Nitrogen was used as inert gas. Five microliters of the paraffin naphtha were injected into the evaporating chamber which was at a temperature of 400° C. The vaporized sample was then diluted with a nitrogen flow of 3 ltr/h (responding with a steam/naphtha ratio in the industrial furnace of 0.7) and propelled into the mono-tubular furnace of capillary dimensions which was at a temperature of 830° C. The cracked products were then examined in four gas-chromatographs.

According to gas chromatographic analysis, the product yield in % by weight of the feed was as follows:

| | | | |
|---|---|---|---|
| $H_2$ | 0.69 | | First Gas Chromatographic Analysis |
| $CH_4$ | 13.34 | | |
| $C_2H_6$ | 5.25 | | |
| $C_2H_4$ | 24.89 | | |
| $C_2H_2$ | 0.31 | | |
| $C_3H_8$ | 0.75 | | |
| $C_3H_6$= | 15.97 | | |
| $C_3H_4$== | 0.23 | | Second Gas Chromatographic Analysis |
| i-$C_4H_{10}$ | 0.14 | | |
| n-$C_4H_{10}$ | 0.73 | | |
| i-$C_4H_8$ | 2.36 | | |
| n-$C_4H_8$ | 2.02 | | |
| trans-$C_4H_8$ | 0.65 | | |
| cis-$C_4H_8$ | 0.52 | | |
| $C_4H_6$-1,3 | 4.52 | | |
| | | 72.37 | |
| Pyrolysis gasoline | 24.31 | — | Third Gas Chromatographic Analysis |
| Pyrolysis fuel oil | 3.32 | — 27.63 | Closing entry |
| Total | | 100.00 | |
| The Analysis For Aromatics Was: | | | Fourth Chromatographic Analysis |
| Benzene | 5.79 | | |
| Toluene | 2.89 | | |
| p-Xylene | 0.18 | | |
| m-Xylene | 0.50 | | |
| o-Xylene | 0.36 | | |
| Ethyl benzene | 0.33 | | |
| Styrene | 0.90 | | |

In an industrial cracking furnace, the same raw material gave virtually the same product range with the industrial furnace being adjusted so that the same "cracking conditions" were realized as in the testing apparatus. "Cracking conditions" as used herein means that the industrial furnace was adjusted so that the yield of one of the cracked products (e.g., $CH_4$) or the ratio betweeen two products (e.g., $C_3/C_2$) was the same as in the testing apparatus. This experiment demonstrates that the method and equipment of the present invention do achieve their intended result. When the same experiment is carried out without the use of an evaporating chamber, which is possible in principle, the results obtained are not comparable to those of an industrial cracking furnace.

What is claimed is:

1. A method for determining the thermal cracking behavior of hydrocarbon feedstocks for industrial cracking furnaces, which method comprises the steps of,
   (a) injecting a liquid sample of the hydrocarbon feedstock into a heated evaporation chamber,
   (b) vaporizing said sample in said chamber,
   (c) diluting said vaporized sample with an inert gas fed into the evaporation chamber forming mixed inert gas/hydrocarbon feedstock vapors which has a partial pressure of the hydrocarbon which corresponds to the partial pressure of the hydrocarbon feedstock in the industrial cracking furnace,
   (d) propelling the said mixed inert gas/hydrocarbon feedstock vapors by means of an inert gas into a mono-turbular furnace of capillary dimensions,
   (e) cracking said diluted vaporized sample into its constituents, and
   (f) analyzing the cracked products.

2. The process of claim 1, wherein the amount of the liquid sample of step (a) is between about 0.5 and 20 microliters.

3. The process of claim 1, wherein the amount of liquid sample of step (a) is about 5 microliters.

4. A method for determining the thermal cracking behavior of hydrocarbon feedstocks for industrial cracking furnace, which method comprises the steps of:
   (a) injecting a gaseous sample of the hydrocarbon feedstock into a heated evaporation chamber,
   (b) diluting said gaseous sample with an inert gas feed into the evaporation chamber forming mixed inert gas/hydrocarbon feedstock vapors which has a partial pressure of the hydrocarbon which corresponds to the partial pressure of the hydrocarbon feedstock in the industrial cracking furnace,
   (c) propelling said mixed inert gas/hydrocarbon feedstock vapors by means of an inert gas into a mono-tubular furnace of capillary dimensions,
   (d) cracking said diluted sample into its constituents, and
   (e) analyzing the cracked products.

5. Apparatus for determining the thermal cracking behavior of hydrocarbon feedstocks for industrial cracking furnaces consisting essentially of,
   a first chamber having
      (i) a fluid inlet and a vapor outlet,
      (ii) first and second inert gas inlets, said first and second gas inlets being respectively positioned adjacent said fluid inlet and vapor outlet, and
      (iii) means for heating and vaporizing the fluid,
   and a second capillary size turbular reactor chamber having
      (i) a vapor inlet connected to said vapor outlet of first said chamber and a vapor outlet, and
      (ii) means for heating the said vapor in said second chamber for thermal cracking of the said vapor, said second chamber being constructed of a catalytically inert material.

6. The apparatus of claim 5, wherein the catalytically inert material is a silicate material.

7. The apparatus of claim 5, wherein the catalytically inert material is a sintered metal compound of carbon.

8. The apparatus of claim 5, wherein the catalytically inert material is a sintered metal compound with silicon.

9. The apparatus of claim 5, wherein the catalytically inert material is a sintered metal compound with carbon and silicon.

10. The apparatus of claim 5, wherein the catalytically inert material is an inactive metal selected from titanium, columbium, gold, zirconium and inactive alloys thereof.

11. The apparatus of claim 5, wherein the catalytically inert material is an inactive alloy of an inactive metal.

12. The apparatus of claim 5, wherein the catalytically inert material is an alloy of a metal group IB of the Periodic Table.

13. The apparatus as in claim 5, wherein said second chamber consists essentially of a tube of catalytically inert material with a diameter ranging between about 0.6 and about 3 mm.

14. The apparatus of claim 13, wherein said second chamber consists essentially of a tube where the diameter is about 1 mm.

15. The apparatus of claim 14, wherein the catalytically inert material is a sintered metal compound with carbon.

16. The apparatus of claim 14, wherein the catalytically inert material is a sintered metal compound with silicon.

17. The apparatus of claim 14, wherein the catalytically inert material is a sintered metal compound with carbon and silicon.

18. The apparatus of claim 14, wherein the catalytically inert material is an inactive metal selected from titanium, columbium, gold, zirconium and inactive alloys thereof.

19. The apparatus of claim 14, wherein the catalytically inert material is an alloy of a metal in group IB of the Periodic Table.